(12) United States Patent
Miyatani

(10) Patent No.: US 9,291,532 B2
(45) Date of Patent: Mar. 22, 2016

(54) AUTOMATIC THIN SECTION SAMPLE PREPARATION DEVICE

(71) Applicant: SAKURA FINETEK JAPAN CO., LTD., Tokyo (JP)

(72) Inventor: Tatsuya Miyatani, Tokyo (JP)

(73) Assignee: SAKURA FINETEK JAPAN CO., LTD., Tokyo (JP)

( * ) Notice: Subject to any disclaimer, the term of this patent is extended or adjusted under 35 U.S.C. 154(b) by 0 days.

(21) Appl. No.: 14/438,053

(22) PCT Filed: Nov. 1, 2013

(86) PCT No.: PCT/JP2013/079707
§ 371 (c)(1),
(2) Date: Apr. 23, 2015

(87) PCT Pub. No.: WO2014/073478
PCT Pub. Date: May 15, 2014

(65) Prior Publication Data
US 2015/0268141 A1 Sep. 24, 2015

(30) Foreign Application Priority Data
Nov. 8, 2012 (JP) ................................ 2012-246335

(51) Int. Cl.
| | |
|---|---|
| *A61B 10/00* | (2006.01) |
| *G01N 1/28* | (2006.01) |
| *G01N 1/06* | (2006.01) |
| *G01N 1/31* | (2006.01) |
| *G01N 35/00* | (2006.01) |
| *G01N 35/10* | (2006.01) |
| *G01N 1/36* | (2006.01) |

(52) U.S. Cl.
CPC ............... *G01N 1/2813* (2013.01); *G01N 1/06* (2013.01); *G01N 1/312* (2013.01); *G01N 35/00029* (2013.01); *G01N 35/00732* (2013.01); *G01N 35/10* (2013.01); *G01N 1/36* (2013.01)

(58) Field of Classification Search
CPC .................................. G01N 1/06; G01N 1/312
See application file for complete search history.

(56) References Cited

U.S. PATENT DOCUMENTS

2010/0030364 A1    2/2010   Fujimoto et al.

FOREIGN PATENT DOCUMENTS

| JP | 2007-212386 | 8/2007 |
|---|---|---|
| JP | 2008-164521 | 7/2008 |
| JP | 4548356 | 7/2010 |
| JP | 2010-185818 | 8/2010 |
| JP | 4674810 | 2/2011 |
| JP | 2012-514201 | 6/2012 |
| WO | 2010/078240 | 7/2010 |

OTHER PUBLICATIONS

International Search Report from corresponding PCT Application No. PCT/JP2013/079707 dated Nov. 26, 2013. English translation attached.

*Primary Examiner* — Jyoti Nagpaul
(74) *Attorney, Agent, or Firm* — Grossman, Tucker, Perreault & Pfleger, PLLC

(57) ABSTRACT

An automatic thin section sample preparation device includes: a reading portion which reads the ID data; a first imaging portion which images a surface image of an embedding block; a sample preparation mechanism which prepares a thin section by thinly cutting the embedding block, fixes the thin section to a substrate, and prepares a thin section sample; a second imaging portion which images a thin section image of the thin section in the thin section sample; a recording portion which records individual data on the substrate in the thin section sample; and a control portion. The control portion includes a determination portion which determines whether or not the thin section is prepared from an original embedding block by collating the surface image and the thin section image, and a storage portion which stores the determination result from the determination portion in association with the ID data, as the individual data.

6 Claims, 4 Drawing Sheets

AUTOMATIC THIN SECTION SAMPLE PREPARATION DEVICE

TECHNICAL FIELD

The present invention relates to an automatic thin section sample preparation device which prepares a thin section by thinly cutting an embedding block including an embedded biological sample, fixes the thin section to a substrate, and prepares a thin section sample.

Priority is claimed on Japanese Patent Application No. 2012-246335, filed Nov. 8, 2012, the content of which is incorporated herein by reference.

BACKGROUND ART

As one method for inspecting and observing a biological sample extracted from a human body, a laboratory animal, or the like, a method is known in which a thin section is prepared from an embedding block in which the biological sample is embedded by an embedding agent, dye processing is performed on the thin section, and thus, the biological sample is observed.

In the related art, an operation of preparing the thin section is performed manually by an experienced operator using a sharp and thin cutting blade. However, in recent years, an automatic thin-cutting device capable of automatically performing the operation of preparing the thin section has begun to be provided. According to this automatic thin-cutting device, it is possible to continuously prepare the thin section without imposing a burden on the operator (refer to Patent Document 1).

Moreover, a thin section sample is prepared by fixing the prepared thin section to a substrate such as a slide glass. In addition, an operator performs pathological inspection or the like while performing dye processing or the like on the thin section in the thin section sample.

However, regardless of the manual preparation method or the automatic preparation method of the thin section, generally, the operator views and compares the thin section in the thin section sample and the embedding block which is the origin of the thin section, and visually performs collation whether or not the thin section is thinly cut from the embedding block, based on the shapes or the like of the thin section and the embedding block. In this case, in order to prevent specimen mix-up, the operator carefully performs the collation operation.

Here, as the automatic thin-cutting device, a device is known which reads ID data printed on a cassette to which an embedding block is fixed and prints the ID data on a slide glass in the thin-section sample (refer to FIG. 2). The operator can easily perform the collation using this device.

CITATION LIST

Patent Literature

[Patent Document 1] Japanese Patent No. 4674810
[Patent Document 2] Japanese Patent No. 4548356

SUMMARY OF INVENTION

Technical Problem

An operator can easily determine an embedding block which is an origin from ID data printed on a slide glass using the device disclosed in Patent Document 2, and thus, the operator can rapidly perform a collation operation. However, also in this case, finally, it is necessary to visually perform the collation between the thin section in the thin section sample and the embedding block by the operator.

That is, since the read ID data is printed only on the slide glass, the device does not understand whether or not the thin section fixed to the slide glass is actually thinly cut from the embedding block in which the ID data is read. Accordingly, as described above, it is still necessary to visually perform the collation operation by the operator.

However, since the visual collation is performed by the operator himself or herself, specimen mix-up may occur due to oversight, collation mistake, or the like. Particularly, it is necessary to visually collate successively the thin sections, which are prepared in large quantities by the automatic thin-cutting device, by the operator, a burden imposed on the operator is increased, the specimen mix-up easily occurs, and advantages of the automation are reduced.

In addition, since only the collation result remains in the visual collation, it is difficult to review and perform verification of the collation operation.

An aspect of the present invention is made in consideration of the above-described circumstances, and an object thereof is to provide an automatic thin section sample preparation device capable of accurately collating and determining whether or not the thin section in the thin section sample is prepared from the embedding block which is the origin, and of performing the verification of the collection operation at arbitrary timing.

Solution to Problem

In order to achieve the object, an aspect according to the present invention adopts the following configurations.

(1) According to an aspect of the present invention, there is provided an automatic thin section sample preparation device that prepares a thin section by thinly cutting an embedding block which includes an embedded biological sample and is held by a cassette to which ID data is attached in advance, fixes the thin section to a substrate, and prepares a thin section sample, the device including: a reading portion configured to read the ID data; a first imaging portion configured to image a surface image of the embedding block; a sample preparation mechanism configured to prepare the thin section by thinly cutting the embedding block, fix the thin section to the substrate, and prepare the thin section sample; a second imaging portion configured to image a thin section image of the thin section in the thin section sample; a recording portion configured to record individual data on the substrate in the thin section sample; and a control portion which is configured to control an operation of the sample preparation mechanism, and to which the ID data read by the reading portion, the surface image imaged by the first imaging portion, and the thin section image imaged by the second imaging portion are input, in which the control portion includes: a determination portion configured to determine whether or not the thin section is prepared from an original embedding block by collating the surface image and the thin section image; and a storage portion configured to store the determination result from the determination portion in association with the ID data, as the individual data.

According to the aspect (1), when the thin-cutting of the embedding block is performed by the sample preparation mechanism, the reading portion reads the ID data and outputs the read ID data to the control portion, and the first imaging portion images the surface of the embedding block and outputs the surface image to the control portion. In addition, when the sample preparation mechanism prepares the thin section by thinly cutting the embedding block, fixes the thin section to the substrate, and prepares the thin section sample, the second imaging portion images the surface of the thin section fixed to the substrate and outputs the thin section image to the control portion.

Then, the determination portion in the control portion collates the received surface image and thin section image, and accurately and rapidly determines whether or not the thin section fixed to the substrate is thinly cut from the embedding block which is the origin, based on both images. In addition, the storage portion stores the determination result from the determination portion in association with the received ID data, as the individual data. Moreover, the recording portion records the individual data on the substrate which is the thin section sample.

Accordingly, since an operator can easily and correctly understand the determination result from the collation operation by only confirming the individual data recorded on the substrate of the thin section sample, it is possible to prevent specimen mix-up. Particularly, unlike to the related art, the collation operation is not performed by a manual operation, throughput is improved, and it is possible to decrease a burden imposed on the operator.

Moreover, since it is possible to confirm the determination result from the collation operation in association with the ID data by confirming the individual data, it is possible to perform verification of the collation operation at arbitrary timing, and thus, ease of use and convenience are increased.

(2) In the aspect (1), the storage portion may store the surface image and the thin section image in association with the ID data in addition to the determination result.

In this case, since it is possible to reconfirm not only the determination result from the collation operation but also two sheets of images of the surface image and the thin section image by confirming the individual data, the verification of the collation operation can be more accurately and easily performed.

(3) In the aspect (1) or (2), the determination portion may perform determination by matching first extraction data where a contour of the biological sample exposed to a surface of the embedding block is extracted from the surface image and second extraction data where a contour of the biological sample exposed to a surface of the thin section is extracted from the thin section image.

In this case, the determination portion performs the determination by matching the contour of the biological sample exposed to the surface of the embedding block and the contour of the biological sample exposed to the surface of the thin section fixed to the surface.

Since the thin section is prepared by thinly cutting the surface of the embedding block, the contour of the biological sample exposed to the surface of the embedding block immediately before the thin-cutting is performed, and the contour of the biological sample exposed to the surface of the thin section are the same as each other or are the ins and outs thereof respectively. Accordingly, it is possible to more accurately perform the collation by performing the matching.

(4) In the aspect (3), the determination portion may perform the determination by extracting geometric characteristics of the biological sample exposed to the surface of the embedding block from the surface image and adding the extracted geometric characteristics to the first extraction data and by extracting geometric characteristics of the biological sample exposed to the surface of the thin section from the thin section image and adding the extracted geometric characteristics to the second extraction data, and by matching the first extraction data and the second extraction data.

In this case, since the determination portion performs the collation operation by adding not only the contour but also the geometric characteristics, it is possible to more accurately perform the collation.

(5) In the aspect (1) or (2), the determination portion may perform determination by matching first extraction data where geometric characteristics of the biological sample exposed to a surface of the embedding block are extracted from the surface image and second extraction data where geometric characteristics of the biological sample exposed to a surface of the thin section are extracted from the thin section image.

In this case, the determination portion performs the determination by matching the geometric characteristics of the biological sample exposed to the surface of the embedding block, and the geometric characteristics of the biological sample exposed to the surface of the thin section fixed to the substrate. As described above, since the thin section is prepared by thinly cutting the surface of the embedding block, the geometric characteristics of the biological sample exposed to the surface of the embedding block immediately before the thin-cutting is performed, and the geometric characteristics of the biological sample exposed to the surface of the thin section are the same as each other or are the ins and outs thereof respectively. Accordingly, it is possible to more accurately perform the collation by performing the matching.

(6) In any one of aspects (1) to (5), the first imaging portion and the second imaging portion may image the surface image and the thin section image using vertical illumination light.

In this case, since the vertical illumination light is used, it is possible to image the surface image and the thin section image in a state where the biological sample is more clearly represented (emphasized). That is, the vertical illumination light is scattered at the portion of the biological sample while the vertical illumination light is mirror-reflected at the portion of the embedding agent such as paraffin. Accordingly, it is possible to generate a difference with respect to the density of the reflected light between the portion of the biological sample and the portion of the embedding agent, and thus, it is possible to more clearly represent the biological sample. Therefore, the determination portion more accurately and easily performs the collation operation based on both images.

Advantageous Effects of Invention

According to the aspects of the present invention, it is possible to accurately collate and determine whether or not a thin section in a thin section sample is prepared from an embedding block which is an origin, and it is possible to perform verification of a collation operation at arbitrary timing.

DESCRIPTION OF EMBODIMENTS

Hereinafter, an embodiment of the present invention will be described with reference to the drawings.

<Configuration of Automatic Thin Section Sample Preparation Device>

Figure 1:
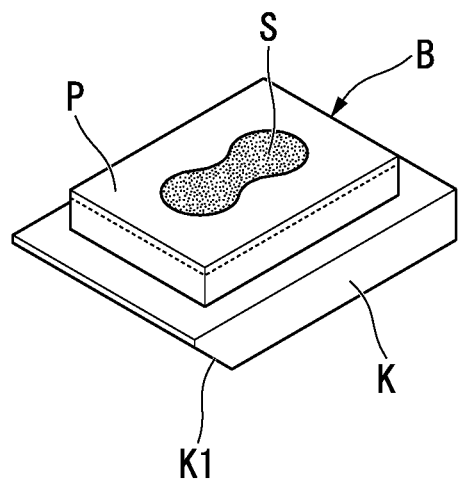
FIG. 1 is a perspective view of an embedding block and a cassette which are used by an automatic thin section sample preparation device according to the present invention.
Figure 2:
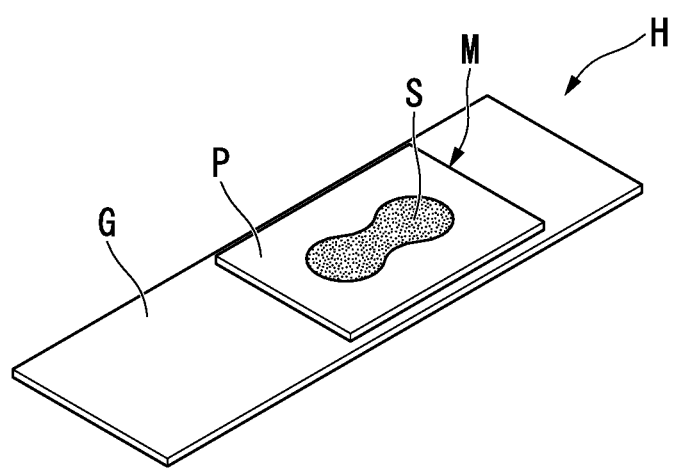
FIG. 2 is a perspective view showing a state where a thin section thinly cut from the embedding block shown in FIG. 1 is fixed to a slide glass and a thin section sample is made.

As shown in FIG. 1, an automatic thin-cutting device (automatic thin section sample preparation device) of the present embodiment is a device which thinly cuts an embedding block B, in which a biological sample S is embedded by a paraffin P serving as an embedding material, to a thickness of 3 μm to 5 μm, for example. Accordingly, it is possible to prepare a thin section M shown in FIG. 2 by the automatic thin-cutting device 1.

In addition, the automatic thin-cutting device of the present embodiment not only can prepare the thin section M but also can automatically perform an operation of accommodating the thin section samples H in a basket after transferring the thin section M to the substrate such as a slide glass G and preparing the thin section samples H.

In addition, in the embedding block B, moisture in the formalin-fixed biological sample S is paraffin-substituted, and thereafter, the periphery is hardened in a block shape by the paraffin P. Accordingly, the biological sample S is embedded in the paraffin P. In addition, for example, the biological sample S is a tissue such as an internal organ extracted from a human body, experimental animal, or the like, and is a tissue which is appropriately selected in a medical field, a pharmaceutical field, a food field, a biological field, or the like.

In addition, as shown in FIG. 1, the embedding block B is fixed to a cassette K.

The cassette K is formed in a box shape by a resin having chemical resistance or the like, and has a role as a fixing table which fixes the embedding block B. One side surface of the cassette K is an inclined surface K1 in which the surface faces downward. ID data (not shown), which includes a production number of the cassette K, a preparation date of the embedding block B, various data of the biological sample S, or the like, is recorded on the inclined surface K1. Accordingly, it is possible to manage quality of the embedding block B by reading the ID data.

Subsequently, each component of the automatic thin-cutting device will be described.

Figure 3:
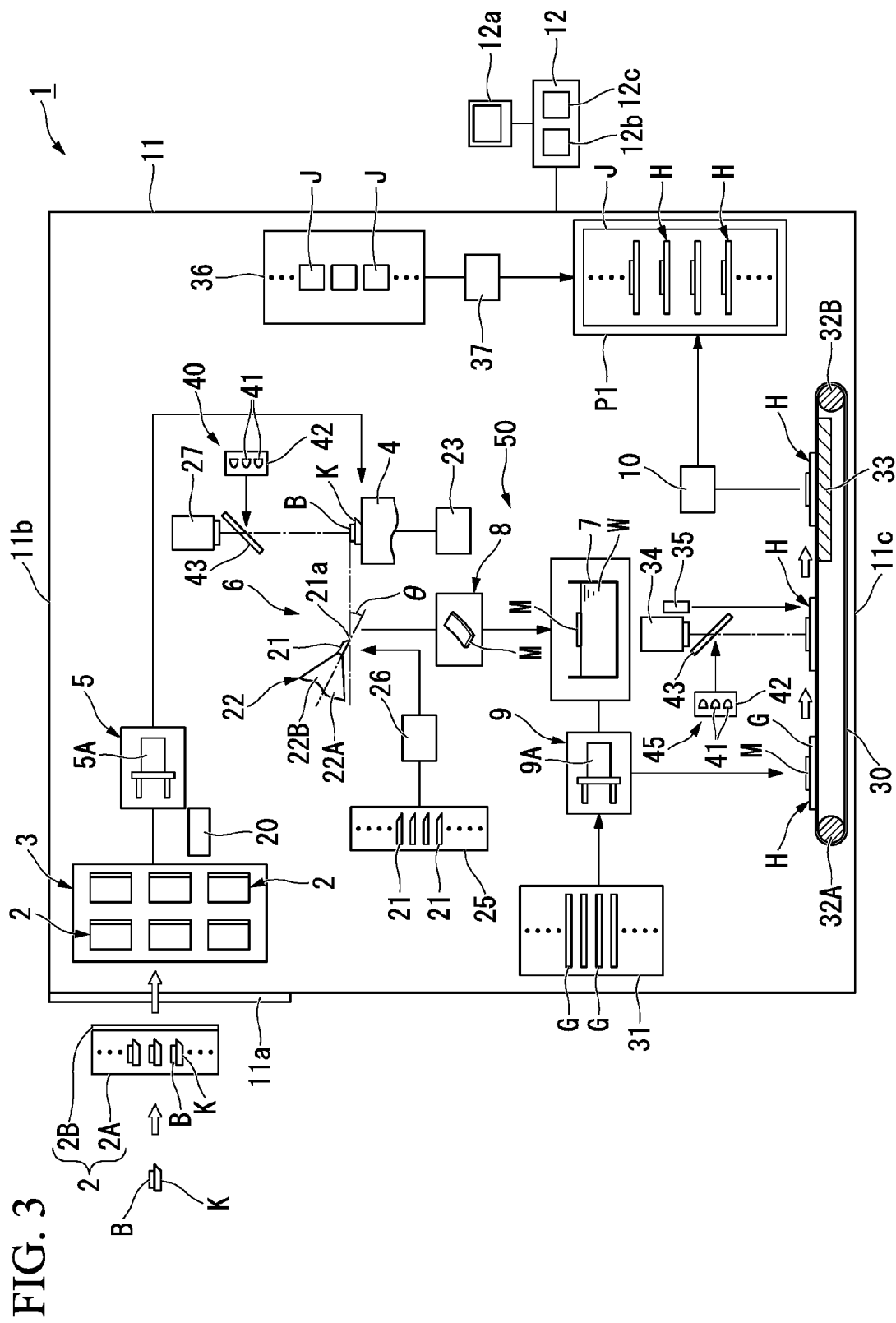
FIG. 3 is a schematic configuration view showing an embodiment of the automatic thin section sample preparation device according to the present invention.

As shown in FIG. 3, the automatic thin-cutting device 1 mainly includes: a plurality of magazines 2 in which the plurality of embedding blocks B are accommodated to be inserted into and removed from the magazines; a carousel 3 which can detachably mount the magazines 2 individually; a block transport mechanism 5 which inserts and removes one embedding block B selected from the plurality of embedding block B accommodated in the magazine 2 mounted on the carousel 3 and places the embedding block on a stage 4 which is a thin-cutting position; a thin-cutting mechanism 6 which cuts the embedding block B placed on the stage 4 at a predetermined thickness and in which the cutting of thin section M is performed; a thin section transport mechanism 8 which transports the thin section M cut by the thin-cutting mechanism 6 to the storage tank 7 and floats the thin section M on a liquid surface to spread the thin section M; a slide glass handling mechanism 9 which scoops the spread thin section M from the liquid surface onto the slide glass G and prepares the thin section sample H; a slide glass accommodation mechanism 10 which accommodates the prepared thin section sample H in a basket J; a device case (housing) 11 which accommodates the components in the inner portion; and a control portion 12 which totally controls the components.

(Device Case)

The inner portion of the above-described device case 11 can be sealed, and for example, in the inner portion, an environmental condition such as humidity, temperature, or the like can be set to a desired condition. An access door 11a which is opened and closed by an operator is provided on the wall surface of the device case 11. The access door 11a is a door which is used when the magazine 2 is mounted or extracted, and by opening the access door 11a, access to the carousel 3 on which the magazine 2 is mounted is possible.

Moreover, in the present embodiment, a top surface 11b side of the device case 11 is defined as a upper side, a bottom surface 11c side is defined as a lower side, and a direction perpendicular to the top surface 11b and the bottom surface 11c is defined as a vertical direction.

(Magazine)

The magazine 2 is an accommodation case in which the entirety is formed in a vertically long rectangular parallelepiped shape, and can accommodate the plurality of embedding blocks B fixed to the cassettes K in a state where the embedding blocks B are arranged in one row along the vertical direction. The magazine 2 mainly includes a box-shaped magazine main body 2A in which the front surface is opened, and an opening and closing door 2B which is fixed to the magazine main body 2A.

When the opening and closing door 2B is closed, a portion of the plurality of embedding blocks B accommodated in the magazine main body 2A is covered, and thus, dropping of the embedding block B is prevented. Accordingly, the operator can deliver the magazine 2 at ease without paying attention to the dropping of the embedding block B.

(Carousel)

The magazine 2 configured as described above can be detachably mounted on the carousel 3. In the illustrated example, six magazines 2 are simultaneously mounted on the carousel 3.

The carousel 3 is disposed at a position at which access is possible from the outside by opening the access door 11a of the device case 11. Accordingly, the magazine 2 can be mounted on the carousel 3 or removed from the carousel 3 manually by the operator.

In addition, the carousel 3 can rotate about a rotation axis extending in the vertical direction, moves the magazine 2 mounted by the rotation in a circumferential direction, and can set one selected magazine 2 to a block extraction position at which the magazine 2 faces the block transport mechanism 5.

Moreover, the operation of the carousel 3 is controlled by the control portion 12. In addition, in FIG. 3, the illustration of the carousel 3 is simplified.

(Reading Portion)

In addition, a reading portion 20 is disposed at a position adjacent to the carousel 3, and the reading portion 20 reads ID data printed on the cassette K of each embedding block B which is accommodated in the magazine 2 set at the block extraction position.

For example, the reading portion 20 and the magazine 2 positioned at the block extraction position are movable relative to each other in a vertical direction, and according to this relative movement, the reading portion 20 can read the ID data printed on the cassette K of all embedding blocks B accommodated in the magazine 2. In addition, the reading portion 20 optically reads the ID data and outputs the read ID data to the control portion 12.

(Block Transport Mechanism)

The block transport mechanism 5 is a handling robot which includes a hand portion 5A capable of holding the cassette K which fixes the embedding block B, and is disposed at the position adjacent to the carousel 3. Based on the instruction from the control portion 12, the block transport mechanism 5 holds one embedding block B, which is accommodated in the magazine 2 set at the block extraction position among the magazines 2 mounted on the carousel 3, by the hand portion 5A, can insert and remove the held embedding block B from the magazine 2, or can place the embedding block on the stage 4.

(Stage)

In the stage 4, an actuator or the like is incorporated into the inner portion, and the stage 4 is configured to appropriately move vertically based on the instruction from the control portion 12. Accordingly, it is possible to adjust the height of the embedding block B placed on the stage 4, and it is possible to thinly cut the embedding block B at a desired thickness (for example, 5 μm).

In addition, the stage 4 is a multi-axial stage in which rotation about the vertical axis and swing about a horizontal axis (two axes) can be performed. Therefore, the stage 4 freely controls the posture of the embedding block B, and can set the direction, the inclination, or the like of the embedding block B to a desired state.

(Thin-Cutting Mechanism)

The thin-cutting mechanism 6 includes a cutting blade 21 which is disposed in the vicinity of the stage 4, a holder 22 which holds the cutting blade 21 in an exchangeable manner, and a moving mechanism 23 which moves the stage 4 with respect to the cutting blade 21 and thinly cuts the embedding block B by the cutting blade 21.

The cutting blade 21 is a long blade in which one end side becomes a blade edge 21a, and is obliquely held (clamp-fixed) to the holder 22 with a predetermined drawn and rake angle θ. In addition, in the illustrated example, the blade edge 21a is a single edge. However, the blade edge may be a double edge.

The holder 22 mainly includes a placing plate 22A on which the cutting blade 21 is placed in a state where the blade edge 21a is exposed to the outside, and a pressing plate 22B which presses the placed cutting blade 21 to the placing plate 22A and in which the cutting blade 21 is clamp-fixed.

The moving mechanism 23 includes a guide rail (not shown) and a driving portion (not shown) which reciprocates the stage 4 along the guide rail at a predetermined speed, thinly cuts the embedding block B by the cutting blade 21 clamp-fixed by the holder 22 by reciprocating the stage 4 based on the instruction from the control portion 12, and performs the cutting of the thin section M.

In addition, the stage 4 raises the embedding block B by a predetermined amount according to the reciprocation by the moving mechanism 23. Accordingly, the embedding block B is cut at a predetermined thickness, and it is possible to prepare the thin section M.

In addition, in the present embodiment, the moving mechanism 23 is configured so that the stage 4 side moves with respect to the cutting blade 21. However, the moving mechanism 23 may be configured so that the cutting blade 21 side moves with respect to the stage 4, or may be configured so that the holder 22 side and the stage 4 side move together.

In either case, the moving mechanism 23 may be designed in any manner as long as the embedding block B and the cutting blade 21 move relative to each other and the thin-cutting can be performed by the cutting blade 21.

(Accommodation Case and Cutting Blade Transport Mechanism)

A plurality of the cutting blades 21 are accommodated in the accommodation case 25 in a state of being overlapped in multi stages, and after the cutting blades 21 are extracted one by one as necessary by the cutting blade transport mechanism 26, the cutting blade 21 is transported to the holder 22 and clamp-fixed. That is, the cutting blade 21 can be replaced at a predetermined timing.

Based on the instruction from the control portion 12, the cutting blade transport mechanism 26 inserts a new cutting blade 21 extracted from the accommodation case 25 into a portion between the placing plate 22A and the pressing plate 22B in the holder 22, and extrudes and transports the used cutting blade 21 from the holder 22.

Accordingly, the replacement of the cutting blade 21 is performed, and the pressing plate 22B of the holder 22 receives the intention that a new cutting blade 21 is set and is operated to perform the clamp-fixing of the new cutting blade 21 according to the instruction of the control portion 12.

In addition, the used cutting blade 21 extruded from the holder 22 is sent to a waste bottle (not shown) or the like via a waste chute (not shown) or the like.

(First Imaging Camera)

A first imaging camera (first imaging portion) 27 which images the surface of the embedding block B placed on the stage 4 is disposed above the stage 4.

The first imaging camera 27 images the surface of the embedding block B using the vertical illumination light irradiated by the vertical illumination system 40, and outputs the imaged surface image to the control portion 12.

(Vertical Illumination System)

The vertical illumination system 40 includes a surface light source (42) in which a plurality of LEDs 41 are disposed in a planar shape, an optical system (not shown) which makes the light irradiated by the surface light source 42 be parallel light, and a half mirror 43 which reflects the parallel light so that the parallel light is incident so as to be approximately perpendicular to the surface of the embedding block B placed on the stage 4, and transmits the light reflected from the embedding block B.

Moreover, the light source may not be the surface light source 42. For example, light from a point light source passes through a pin hole, a collimating lens, or the like so as to be parallel light.

(Thin Section Transport Mechanism)

Based on the instruction from the control portion 12, the thin section transport mechanism 8 is a mechanism which transports the thin section M cut by the thin-cutting mechanism 6 up to the storage tank 7 and floats the thin section M on the liquid surface, and for example, the thin section transport mechanism 8 may transport the thin section using a transport belt, a transport tape, or the like, or may transport the thin section using a robotic hand, or the like.

(Storage Tank)

A liquid W such as water which is adjusted to a predetermined temperature is stored in the storage tank 7, and the thin section M floated on the liquid surface is spread by the liquid using a surface tension. In addition, the stored liquid W is discharged from the storage tank 7 via a circulation pipeline (not shown) as necessary, and is supplied into the storage tank 7. Accordingly, a clear liquid W is stored in the storage tank 7 at all times.

(Slide Glass Handling Mechanism)

The slide glass handling mechanism 9 is a handling robot which includes the hand portion 9A capable of holding the slide glass G, and is disposed at a position adjacent to the storage tank 7. Moreover, the slide glass handling mechanism 9 is operated based on the instruction from the control portion 12 and scoops the spread thin section M floated on the liquid surface on the slide glass G held by the hand portion 9A to transfer the thin section M, and thus, it is possible to prepare the thin section sample H.

After the slide glass handling mechanism 9 scoops the thin section M on the slide glass G and prepares the thin section sample H, the slide glass handling mechanism 9 delivers the thin section sample H onto a sample transport belt 30. Thereafter, the slide glass handling mechanism 9 holds a new slide glass G among the slide glasses G accommodated in a slide glass accommodation portion 31 and moves the new slide glass G to a standby state for scooping the next thin section M.

The slide glass accommodation portion 31 is disposed in the vicinity of the storage tank 7, and for example, several dozen to several hundred unused slide glasses G are accommodated in the inner portion of the slide glass accommodation portion 31.

Moreover, the thin-cutting mechanism 6, the thin section transport mechanism 8, the storage tank 7, and the slide glass handling mechanism 9 function as a sample preparation mechanism 50 which thinly cuts the embedding block B, prepares the thin section M, fixes the thin section M to the slide glass G, and prepares the thin section sample H.

(Sample Transport Belt and Hot Plate)

For example, the above-described sample transport belt 30 is an endless belt which is wound between a driving pulley 32A which is driven based on the instruction from the control portion 12 and a driven pulley 32B, and the above-described sample transport belt 30 can transport the thin section sample H to the downstream side by driving of the driving pulley 32A.

The hot plate 33 which is heated to a predetermined temperature is disposed on the downstream side of the sample transport belt 30, and the hot plate heats the thin section sample H placed on the sample transport belt 30 in a state where the thin section sample H is interposed between the hot plate 33 and the sample transport belt 30. Accordingly, superfluous liquid W remaining on the thin section sample H can be removed by vaporization, and it is possible to further spread the thin section M while preventing the existence of the liquid W between the slide glass G and the thin section M.

(Second Imaging Camera and Recording Portion)

Moreover, in the present embodiment, while the thin section sample H is transported up to the downstream side at which the hot plate 33 is disposed by the sample transport belt 30, the imaging of the thin section M using a second imaging camera (second imaging portion) 34 and the printing of individual data to the slide glass G using a recording portion 35 are performed.

The second imaging camera 34 is disposed above the sample transport belt 30, images the thin section M until the thin section sample H placed on the sample transport belt 30 is transported to the downstream side, and sends the thin section image to the control portion 12.

Moreover, similar to the first imaging camera 27, the second imaging camera 34 images the thin section image using the vertical illumination light irradiated by a vertical illumination system 45. Similar to the vertical illumination system 40, the vertical illumination system 45 is configured of the surface light source 42, the optical system (not shown), and a half mirror 43, and thus, descriptions thereof are omitted.

For example, the recording portion 35 is a laser marker and is disposed to be adjacent to the second imaging camera 34, and based on the instruction from the control portion 12, the recording portion 35 irradiates the slide glass G with laser light and performs the printing of the individual data. In this case, similar to the second imaging camera 34, the recording portion 35 performs the printing until the thin section sample H is transported to the downstream side.

(Slide Glass Accommodation Mechanism)

The slide glass accommodation mechanism 10 is disposed above the sample transport belt 30 and is a mechanism which accommodates the thin section sample H on the sample transport belt 30 heated by the hot plate 33 in the basket J, based on the instruction from the control portion 12. For example, as this mechanism, the thin section sample H is extruded from the sample transport belt 30 using an extrusion rod driven by a cylinder or the like and may be stored in the basket J, or the thin section sample H may be accommodated in the basket J using a robotic hand or the like.

(Basket)

For example, the basket J is a dye basket and can accommodate several thin section samples H to several dozen thin section samples H at once, and the plurality of baskets J are stored in a basket accommodation portion 36 in advance. After the baskets J accommodated in the basket accommodation portion 36 are sequentially extracted by a basket supply mechanism 37 which is operated based on the instruction from the control portion 12, the baskets J are set at a sample accommodation position P1. Moreover, at the sample accommodation position P1, the thin section samples H are accommodated in the basket J.

In addition, when the thin section samples H having the predetermined number of sheets are accommodated in the basket J, the basket J is sent into a storage cabinet (not shown) so as to be stored. In this case, warm wind adjusted to a predetermined temperature circulates through the storage cabinet, and thus, the thin section samples H are dried at an optimal state.

(Control Portion)

The control portion 12 totally controls the above-described components, and the ID data read by the reading portion 20, the surface image of the embedding block B imaged by the first imaging camera 27, and the thin section image of the thin section M in the thin section sample H imaged by the second imaging camera 34 are input to the control portion 12.

Moreover, the control portion 12 includes a monitor 12a which appropriately displays the received surface image and thin section image, a determination portion 12b which collates the surface image after the flattening of the embedding block B is completed among the received surface images and the thin section image and determines whether or not the thin section M is prepared from the original embedding block B, and a memory portion (storage portion) 12c which stores the determination result from the determination portion 12b in association with the ID data, as the individual data.

<Operation of Automatic Thin Section Sample Preparation Device>

Next, the operation of the automatic thin-cutting device 1 configured as described above will be described.

Moreover, in the present embodiment, first, the overall flow until the thin section sample H is prepared is simply described, and thereafter, the flow of the partial process will be described in detail.

First, as advance preparation, after the operator accommodates cassettes K, to which embedding blocks B are fixed, in the plurality of magazines 2, the operator opens the access door 11a of the device case 11, and mounts the magazines 2 on the carousel 3. After each magazine 2 is mounted on the carousel 3, the access door 11a is closed. In addition, the operator confirms whether or not the cutting blade 21 is appropriately set into the accommodation case 25, whether or not the slide glass G is appropriately set to the slide glass accommodation portion 31, whether or not the basket J is appropriately set to the basket accommodation portion 36, or the like, and thus, the advance preparation ends.

After the advance preparation ends, the operator starts the operation of each component in the device case 11 through the control portion 12.

Then, the control portion 12 sequentially rotates the carousels 3 and reads the ID data by the reading portion 20, and thereafter, the embedding blocks B are held using the hand portions 5A by the block transport mechanism 5. Subsequently, after the held embedding block B is extracted from the magazine 2 by the block transport mechanism 5, the embedding block B is placed on the stage 4 via the cassette K.

When the setting operation of the embedding block B on the stage 4 ends, the control portion 12 starts the thin-cutting operation of the embedding block B.

First, the upper surface of the embedding block B is adjusted to a desired height position by adjusting the height of the stage 4. In addition, the moving mechanism 23 reciprocates the stage 4 in the thin-cutting mechanism 6, and thus, the embedding block B is thinly cut by the cutting blade 21 which is clamped-fixed by the holder 22. Accordingly, it is possible to perform rough-flattening of the embedding block B.

When the thin-cutting is performed, the first imaging camera 27 images the surface of the embedding block B. The imaged surface image is sent to the control portion 12 and is displayed on the monitor 12a.

Accordingly, the operator can incline or rotate the appropriate stage 4 during the thin-cutting, with reference to the surface image which is displayed on the monitor 12a. As a result, it is possible to expose an optimal surface to the surface by rough machining of the embedding block B.

In addition, when a flattening operation is performed by the above-described rough machining, the operation in which the thin section M is transported to the storage tank 7 by the thin section transport mechanism 8 is not performed. Accordingly, the thin section M generated in the case becomes cutting debris and is recovered to a recovery portion (not shown).

Subsequently, after the flattening of the embedding block B ends, the control portion 12 transfers the operation of the automatic thin-cutting device 1 from the rough machining operation to a main cutting operation. In this case, the control portion 12 operates the cutting blade transport mechanism 26 and replaces the cutting blade 21 used in the rough machining with a new cutting blade 21. Moreover, the replacement of the cutting blade 21 is not limited to this case and may be appropriately performed if necessary.

When the operation is transferred to the main cutting operation, the control portion 12 prepares the thin section M by the thin-cutting mechanism 6, transports the prepared thin section M to the storage tank 7 by the thin section transport mechanism 8, and floats the thin section on the liquid surface. Accordingly, the thin section M is spread, and curling or the like generated during the thin-cutting is removed.

Subsequently, the control portion 12 operates the slide glass handling mechanism 9, scoops the thin section M floated on the liquid surface onto the slide glass G, and prepares the thin section sample H. The slide glass handling mechanism 9 places the prepared thin section sample H on the sample transport belt 30 and delivers the thin section sample H.

Moreover, the control portion 12 drives the driving pulley 32A, and transports the thin section sample H placed on the sample transport belt 30 toward the downstream side. Then, while the thin section sample H is transported to the hot plate 33, the second imaging camera 34 images the thin section M, and the thin section image is sent to the control portion 12.

Based on the thin section image received from the second imaging camera 34, the control portion 12 determines whether or not the thin section M subjected to the main cutting is appropriately cut thinly. Here, when the control portion 12 determines that the thin-cutting is good, the control portion 12 operates the recording portion 35, and the individual data associated with the ID data read from the cassette K is recorded in the slide glass G of the thin section sample H.

In addition, the thin section sample H in which the individual data is recorded is further transported to the downstream side of the sample transport belt 30 and is heated by the hot plate 33. Moreover, the control portion 12 operates the slide glass accommodation mechanism 10 and accommodates the heated thin section sample H in the basket J.

As the determination result with respect to the quality of thin-cutting, when the control portion 12 determines that the thin-cutting is not good, the control portion 12 does not operate the slide glass accommodation mechanism 10 and delivers the thin section sample H from the sample transport belt 30 to a defective product discharging chute (not shown). Accordingly, the thin section sample H which is the defective product is not accommodated in the basket J, and is recovered.

When the thin section samples H which are determined as good products are accommodated in the basket J in a predetermined number, the basket J is sent to the storage cabinet and is stored, the basket supply mechanism 37 extracts a new basket J from the basket accommodation portion 36 and sets the new basket J at the sample accommodation position P1, and all subsequent accommodation operations are prepared.

As described above, according to the automatic thin-cutting device 1 of the present embodiment, not only the thin section M is automatically prepared but also the thin section sample H is automatically prepared, and it is possible to accommodate the thin section samples H in the basket J in a predetermined number.

Accordingly, the operator extracts the appropriate basket J from the storage cabinet, can transfer the basket J to the dyeing process of the biological sample S as it is, and the basket J is remarkably easily used. Particularly, since it is possible to collect the thin section samples H, in which the same dyeing operation is performed, in the same basket J, great convenience is obtained.

In the automatic thin-cutting device 1 of the present embodiment, in the above-described processes, the determination portion 12b in the control portion 12 performs the operation of collating the surface image after the flattening of the embedding block B is completed among the surface images received from the first imaging camera 27, and the thin section image received from the second imaging camera 34.

Moreover, before the determination portion 12b performs the collation, the determination portion 12b determines whether or not the thin section M mainly cut is appropriately thinly cut based on the thin section image received from the second imaging camera 34, and when it is determined that the thin section is a good product, the determination portion 12b performs the collation operation.

As the collation operation, the determination portion 12b compares the exposure states of the thin sections M projected to the two sheets of images of the surface image and the thin section image, and accurately and rapidly determines whether or not the thin section M fixed to the slide glass G is thinly cut from the embedding block B which is the origin.

The collation operation will be described in detail.

Figure 4:
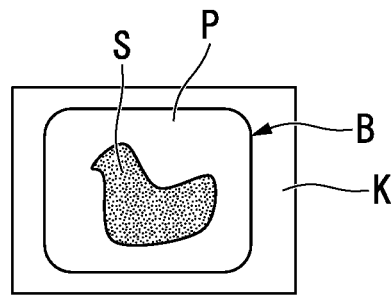
FIG. 4 is a view showing the surface state of the embedding block in which flattening is completed.
Figure 5:
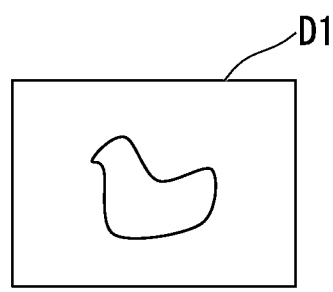
FIG. 5 is a view showing first extraction data generated by extracting a contour of a biological sample from a surface image in which the surface of the embedding block shown in FIG. 4 is imaged.

When the surface state of the embedding block B after the flattening is completed is a state shown in FIG. 4, the determination portion 12b generates first extraction data D1 shown in FIG. 5, in which the contour of the biological sample S exposed to the surface of the embedding block B is extracted, from the surface image received from the first imaging camera 27.

Figure 6:
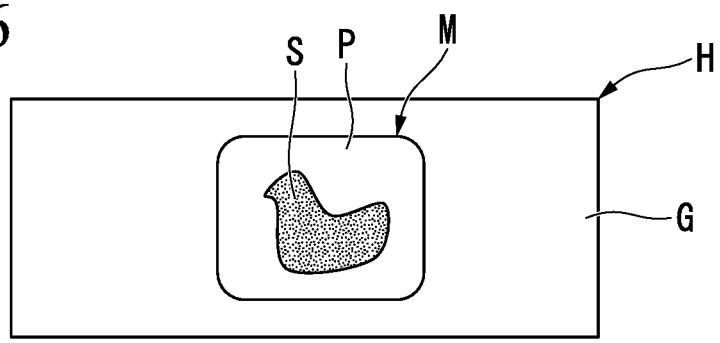
FIG. 6 is a top view of the thin section sample having the thin section obtained by preparing the embedding block shown in FIG. 4.
Figure 7:
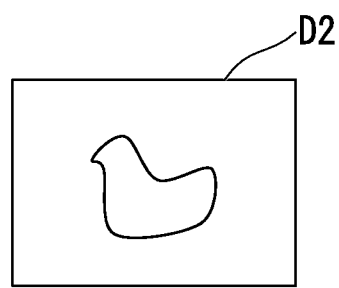
FIG. 7 is a view showing second extraction data generated by extracting a contour of a biological sample from a thin section image in which the surface of the thin section in the thin section sample shown in FIG. 6 is imaged.

Subsequently, the determination portion 12b generates second extraction data D2 shown in FIG. 7, in which the contour of the biological sample S exposed to the surface of the thin section M is extracted, from the thin section image received from the second imaging camera 34 which images the thin section M in the thin section sample H shown in FIG. 6.

Moreover, the determination portion 12b performs the collation by matching the first extraction data D1 and the second extraction data D2, and when the first extraction data is coincident with the second extraction data, the determination portion determines that the thin-cutting is performed from the embedding block B which is the origin, and when the first extraction data is not coincident with the second extraction data, the determination portion determines that the thin-cutting is not performed from the embedding block B which is the origin.

Moreover, as an example when the first extraction data is not coincident with the second extraction data, for example, there is a case where the thin section M is thinly cut from another embedding block B set immediately before the thin cutting is performed, or the like.

When the determination result comes out, the memory portion 12c sets the determination result in association with the ID data received from the reading portion 20 to the individual data, and stores the individual data. Moreover, as described above, the recording portion 35 records the individual data on the slide glass G in the thin section sample H.

Accordingly, since the operator can easily and correctly understand the determination result from the collation operation by only confirming the individual data recorded on the slide glass G of the thin section sample H, it is possible to prevent specimen mix-up.

Particularly, unlike to the related art, the collation operation is not performed by a manual operation, throughput is improved, and it is possible to decrease a burden imposed on the operator. Moreover, since it is possible to confirm the determination result from the collation operation in association with the ID data by confirming the individual data, it is possible to perform verification of the collation operation at arbitrary timing, and thus, ease of the use and convenience are increased.

As described above, according to the automatic thin-cutting device 1 of the present embodiment, the process is automatically performed in which the thin section M is fixed to the slide glass G and the thin section sample H is prepared after the thin section M is prepared by thinly cutting the embedding block B, and it is possible to accommodate the thin section samples H in the basket J in a predetermined number.

In addition, even when the plurality of embedding blocks B are used, it is possible to prepare the thin section sample H while accurately collating and determining whether or not the thin section M in the thin section sample H is prepared from the embedding block B which is the origin. In addition, the operator can perform verification of the collation operation at arbitrary timing.

Particularly, the determination portion 12b performs the determination by matching the first extraction data D1 and the second extraction data D2. Here, since the thin section M is prepared by thinly cutting the surface of the embedding block B, the contour of the biological sample S exposed to the surface of the embedding block B immediately before the thin-cutting is performed, and the contour of the biological sample S exposed to the surface of the thin section M are the same as each other or are the ins and outs thereof respectively.

Accordingly, it is possible to more accurately perform the collation by performing the matching using the contour.

In addition, when the surface image and the thin section image are imaged, since the vertical illumination light is used, it is possible to image the biological sample S in a state where the biological sample S is more clearly represented (emphasized). That is, the vertical illumination light is scattered at the portion of the biological sample S while the vertical illumination light is mirror-reflected at the portion of the paraffin P which is the embedding agent. Accordingly, it is possible to generate a difference with respect to the density of the reflected light between the portion of the biological sample S and the portion of the paraffin P, and thus, it is possible to more clearly represent the biological sample S. Therefore, the determination portion 12b more accurately and easily performs the collation operation based on both images.

In addition, in the embodiment, when the contour is extracted, the extraction method is not limited to the specific method.

For example, the extraction may be performed using binarization by brightness. Moreover, differentiation is performed to the brightness from the outside of the image toward the center, an initial point in which the differential value exceeds a threshold value is detected as an edge, and the contour of the biological sample S may be extracted by connecting the points.

In addition, in the embodiment, as the result of the collation operation, when the determination portion 12b determines that the thin section M is not coincident with the embedding block B (determines that the thin section M is not thinly cut from the embedding block B), the thin section sample H having the thin section M may be discarded.

Moreover, the technical scope of the present invention is limited to the above-described embodiment, and various modification examples are applied to the above-described embodiment within a scope which does not depart from the gist of the present invention.

For example, in the above-described embodiment, the case where six magazines 2 are mounted on the carousel 3 is described. However, the number of the magazines 2 is not limited to the case. For example, the number of the magazines 2 which are simultaneously mounted on the carousel 3 may be set to an arbitrary number such as one, two, three, four, five, or seven or more.

Moreover, in the embodiment, the memory portion 12c may also store the two sheets of images of the surface image and the thin section image in association with the ID data, in addition to the determination result from the determination portion 12b. In this case, since it is possible to reconfirm not only the determination result from the collation operation but also two sheets of images by confirming the individual data recorded on the slide glass G in the thin section sample H, the verification of the collation operation can be more accurately and easily performed.

Moreover, in the embodiment, the determination portion 12b may perform the collation operation by adding not only the contour but also the geometric characteristics.

Figure 8:
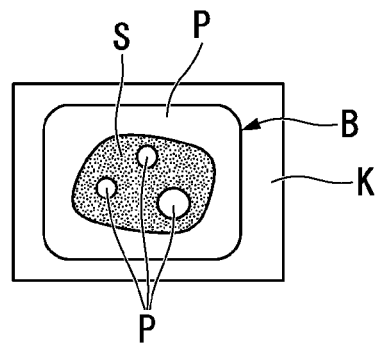
FIG. 8 is a view showing the surface state of an embedding block of a modification example in which flattening is completed.
Figure 9:
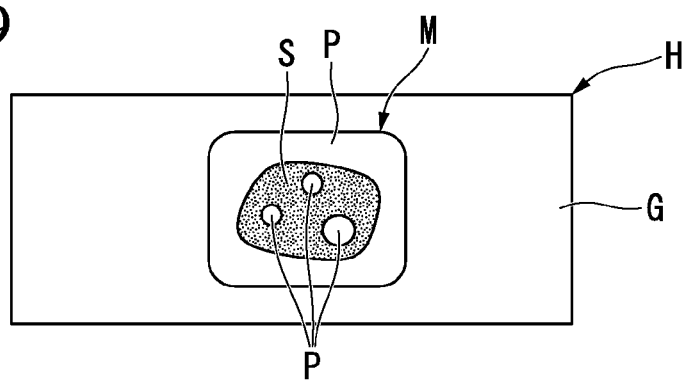
FIG. 9 is a top view of a thin section sample having a thin section obtained by preparing the embedding block shown in FIG. 8.

For example, in a case where blood vessels, tubular organs, or the like are included in the biological sample S, when paraffin substitution is performed, the paraffin P enters the blood vessels or organs. Accordingly, the surface state of the embedding block B after the flattening is completed becomes the state shown in FIG. 8, and the inner portion of the biological sample S is dotted with the paraffin P. Similarly, as shown in FIG. 9, the inner portion of the biological sample S of the thin section M in the thin section sample H is also dotted with the paraffin P.

Figure 10:
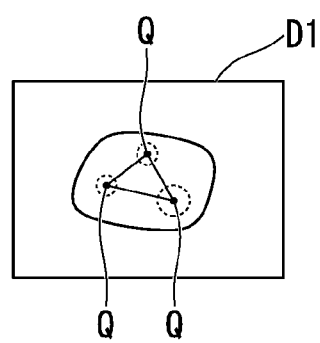
FIG. 10 is a view showing first extraction data generated by extracting a contour and geometric characteristics of the biological sample from the surface image in which the surface of the embedding block shown in FIG. 8 is imaged.

In this case, as shown in FIG. 10, the determination portion 12b generates the first extraction data D1 by extracting the geometric characteristics Q of the biological sample S, in addition to extracting the contour of the biological sample S exposed to the surface of the embedding block B, from the surface image received from the first imaging camera 27.

Figure 11:
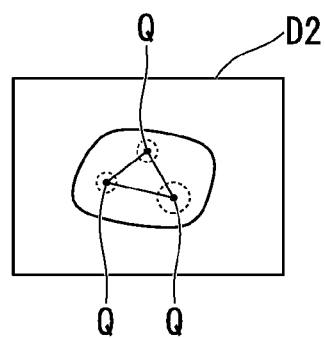
FIG. 11 is a view showing second extraction data generated by extracting the contour and the geometric characteristics of the biological sample from the thin section image in which the surface of the thin section in the thin section sample shown in FIG. 9 is imaged.

Moreover, as shown in FIG. 11, the determination portion 12b generates the second extraction data D2 by extracting the geometric characteristics Q of the biological sample S, in addition to extracting the contour of the biological sample S exposed to the surface of the thin section M, from the thin section image received from the second imaging camera 34.

In addition, the determination portion 12b performs the collation by matching the first extraction data D1 and the second extraction data D2. That is, the collation is performed by performing the matching between the contours and the matching between the disposition patterns of the geometric characteristics Q.

In this case, since the collation operation is performed by adding not only the contour but also the geometric characteristics Q, more preferably, it is possible to more accurately perform the collation.

In addition, the collation operation is performed by adding the geometric characteristics to the contour. However, the present invention is not limited to this, and the determination portion 12 may perform the collation operation by matching the disposition patterns of the geometric characteristics.

That is, the determination portion 12 generates the first extraction data by extracting the geometric characteristics Q of the biological sample S from the surface image received from the first imaging camera 27, generates the second extraction data by extracting the geometric characteristics Q of the biological sample S from the thin section image received from the second imaging camera 34, and may perform the collation operation by matching the disposition patterns of both geometric characteristics Q.

Also in this case, effects similar to those when the contours are matched to each other can be exerted. Moreover, according to the condition of the biological sample S, whether or not the collation operation is performed by the matching of the contours, whether or not the collation operation is performed by the matching of the geometric characteristics, or whether or not the collation operation is performed by the matching of the contours and the geometric characteristics may be appropriately determined Reference Signs List B . . . embedding block, G . . . slide glass (substrate), H . . . thin section sample, K . . . cassette, Q . . . geometric characteristic, S . . . biological sample, D1 . . . first extraction data, D2 . . . second extraction data, 1 . . . automatic thin-cutting device (automatic thin section sample preparation device), 12 . . . control portion, 12b . . . determination portion, 12c . . . memory portion (storage portion), 20 . . . reading portion, 27 . . . first imaging camera (first imaging portion), 34 . . . second imaging camera (second imaging portion), 35 . . . recording portion, 50 . . . sample preparation mechanism

The invention claimed is:

1. An automatic thin section sample preparation device that prepares a thin section by thinly cutting an embedding block which includes an embedded biological sample and is held by a cassette to which ID data is attached in advance, fixes the thin section to a substrate, and prepares a thin section sample, the device comprising:
   a reading portion configured to read the ID data;
   a first imaging portion configured to image a surface image of the embedding block;
   a sample preparation mechanism configured to prepare the thin section by thinly cutting the embedding block, fix the thin section to the substrate, and prepare the thin section sample;
   a second imaging portion configured to image a thin section image of the thin section in the thin section sample;
   a recording portion configured to record individual data on the substrate in the thin section sample; and
   a control portion which is configured to control an operation of the sample preparation mechanism, and to which the ID data read by the reading portion, the surface image imaged by the first imaging portion, and the thin section image imaged by the second imaging portion are input,
   wherein the control portion includes
   a determination portion configured to determine whether or not the thin section is prepared from an original embedding block by collating the surface image and the thin section image, and
   a storage portion configured to store the determination result from the determination portion in association with the ID data, as the individual data.

2. The automatic thin section sample preparation device according to claim 1,
   wherein the storage portion stores the surface image and the thin section image in association with the ID data in addition to the determination result.

3. The automatic thin section sample preparation device according to claim 1,
   wherein the determination portion performs determination by matching first extraction data where a contour of the biological sample exposed to a surface of the embedding block is extracted from the surface image and second extraction data where a contour of the biological sample exposed to a surface of the thin section is extracted from the thin section image.

4. The automatic thin section sample preparation device according to claim 3,
   wherein the determination portion performs the determination by extracting geometric characteristics of the biological sample exposed to the surface of the embedding block from the surface image and adding the extracted geometric characteristics to the first extraction data and by extracting geometric characteristics of the biological sample exposed to the surface of the thin section from the thin section image and adding the extracted geometric characteristics to the second extraction data, and by matching the first extraction data and the second extraction data.

5. The automatic thin section sample preparation device according to claim 1,
   wherein the determination portion performs determination by matching first extraction data where geometric characteristics of the biological sample exposed to a surface of the embedding block are extracted from the surface image and second extraction data where geometric characteristics of the biological sample exposed to a surface of the thin section are extracted from the thin section image.

6. The automatic thin section sample preparation device according to claim 1,
   wherein the first imaging portion and the second imaging portion image the surface image and the thin section image using vertical illumination light.

\* \* \* \* \*